United States Patent [19]

Yancey

[11] 4,257,689

[45] Mar. 24, 1981

[54] PULSE PATTERN VISUAL ACUITY DEVICE

[76] Inventor: Don R. Yancey, chateau Brown 305, 6-26-38, Kita-Karasuyama, Setagaya-ku, Tokyo 157, Japan

[21] Appl. No.: 58,025

[22] Filed: Jul. 16, 1979

[51] Int. Cl.³ .................. A61B 3/10; G01N 21/41
[52] U.S. Cl. ............................. 351/13; 351/39; 356/128
[58] Field of Search .............. 351/13, 39; 356/128

[56] References Cited

U.S. PATENT DOCUMENTS

| | | | |
|---|---|---|---|
| 3,136,839 | 6/1964 | Safir. | |
| 3,715,166 | 2/1973 | Leighty et al. | 351 6 X |
| 3,791,719 | 2/1974 | Kratzer et al. | 351/39 X |
| 3,819,256 | 6/1974 | Bellows et al. | 351/13 X |
| 3,824,005 | 7/1974 | Woestman | 351/13 X |
| 3,843,240 | 10/1974 | Cornsweet | 351/13 X |
| 3,888,569 | 6/1975 | Munnerly et al. | 351/39 X |
| 4,021,102 | 5/1977 | Iizuka | 351/13 |

Primary Examiner—Paul A. Sacher

[57] ABSTRACT

A visual acuity device measures the visual acuity of a patient's eye by directing a pulsating beam of light on the eye and detecting the resulting reflection. A primary pattern having a pattern formed by transparent and non-transparent portions is positioned in the optical path of the pulsating beam of light. A fixed pair of analyzer or secondary pattern is positioned in the optical path of the beam of light reflected from the patient'eye. One of these analyzer or secondary patterns has a pattern which substantially corresponds to the pattern of the primary fixation pattern and the other has a pattern which is the negative mirror image of the pattern of the first analyzer or secondary pattern. The beam of light reflected from the patient's eye is divided by a beam splitter so that each of the analyzer patterns receives the reflected image of the primary pattern from the patient's eye. A photoelectric device is associated with each of the analyzer patterns for detecting the reflected beam of light passing through each of these analyzer patterns to generate an electrical output signal. The photoelectric devices are connected to a difference amplifier for eliminating any glare and generating a signal which is determinative of the visual acuity of the patient's eye. Far visual acuity can be measured by using infrared light adding a collimating and compensating lens. Thus, the visual acuity device objectively measures both far and near visual acuity.

34 Claims, 20 Drawing Figures

NEAR VISION ACUITY OPTICAL SYSTEM

FIG. 3

FAR VISION ACUITY OPTICAL SYSTEM

PRIMARY
PATTERN
(A)

ANALYZER
PATTERN
(B)

PULSE PATTERN VISUAL ACUITY DEVICE

BACKGROUND OF THE INVENTION

The present invention is directed to a device for automatically measuring both the near and far visual acuity of a patient's eyes in a simple and objective manner.

At the present time, there are basically two method for measuring the visual acuity of the eyes. One of these methods utilizes information provided by the person being tested (subjective testing) and the other method uses external measuring devices (objective testing). In the subjective method, vision testers such as charts, etc. have been widely used for many years. However, these vision testers provide no accurate measurement because they rely on the personal evaluation of the patient in comparing the images of a target while various corrective lenses are placed in front of the eyes.

Subjective tests are particularly unsuitable for measuring the visual acuity of children's eyes. For example, this year in the United States, over 2½ million six year old children will enter more than 60,000 elementary schools. The American Association for the Prevention of Blindness estimates that one out of every twenty preschool children has a vision problem which, if uncorrected, will interfere with the child's development and education. Young children are unable to subjectively determine whether their vision is "good"or "bad". These young children cannot respond to conventional chart tests because they cannot read. Special devices such as the Landolt C and Pointing E are used to test the visual acuity of children. Since all these tests are subjective, special training and high motivation are necessary in order to obtain accurate measurements. Consequently, subjective testing methods are difficult to administer, unreliable, time-consuming, and totally impractical for mass vision testing of preschool children.

Objective testing methods are much more effective in measuring the visual acuity of the eyes, particularly the eyes of children. Although automatic objective measuring devices are now available on the market, these devices are not practical for mass vision testing. Existing devices must be operated by trained specialists, usually optometrists or ophthalmologists and they generally are large pedestal mounted devices which occupy a great amount of space and are not portable. Also, since these existing objective devices are complex mechanisms with considerable electronics, the price of these devices is prohibitively high.

As a result of these disadvantages of the existing objective devices, visual acuity is often determined through the use of Snellen letter chart in which the threshold letter size for the subject is found and converted to a visual acuity measurement. This procedure is subject to several subtle variables which can significantly affect the outcome. For example, inappropriate room lighting, test lamp aging, failure of the examinee to cover each eye properly, examiner recording error and inherent testing pressures all affect the visual acuity measurement. Furthermore, the results of such a visual acuity measurement again are often seriously effected by the desires of the patient. Thus, it is often difficult to ascertain the visual acuity of the patient using such charts and other similar subjective devices.

A number of objective devices have been proposed which overcome some of the disadvantages of the subjective devices but which do not overcome all the previously mentioned disadvantages of the objective devices. In U.S. Pat. No. 3,824,005 issued to Westman on July 16, 1974, a refractometer is shown in which the eye observes a target image and the reflected light from the retina of the patient's eye is transformed into an electrical signal that reaches a peak when the target image on the retina is in focus. The apparatus includes a primary bar or target which is illuminated by a light source and observed by the patient's eye through various lenses. The target image formed on the retina is reflected via a beam splitter to a photodetector which is connected to a circuit arrangement to generate an electrical signal related to the visual acuity of the eye. A secondary bar pattern, which is identical to the primary target pattern is positioned between the beam splitter and the photodetector and vibrated by a vibrator to periodically block and unblock the reflected target image from the retina of the patient's eye. When the patient's eye is in focus on the primary target pattern and the secondary bar pattern is not in a blocking position, the intensity of the light detected by the photodetector is at a maximum. In addition, the primary target pattern is constantly moved toward and away from the patient's eye to permit the image of the primary target pattern to be periodically in focus on the retina of the eye regardless of its refracted state. As a result, the measurement of the position of the axially moving primary target at the instant the amplitude of the light transmitted through the secondary bar pattern is at its maximum will provide an indication of the refractive state of the patient's eye.

Another prior art system is shown in U.S. Pat. No. 3,888,569 issued to Munnerly et al. on June 10, 1975 in which a refractometer is shown having an adjustable compensating lens system for focusing the target image on the retina of the eye. The primary target pattern in the Munnerly patient is movable and the secondary pattern positioned adjacent the photodetector is fixed. The signal received by the photodetector is a function of the focus of the image of the primary target pattern on the retina of the eye. A sharply focused bar pattern produces a less intense signal. The visual acuity of the patient's eye is calculated by a computer which controls the focus and position of the patterns and selects and stores results from the signal detected by the photodetector. A compensating lens system is also provided in the Munnerly patent which is controlled by the digital computer and used to adjust the focus of the patient's eye.

Several prior art patents show refractometers and other visual acuity measuring devices which include a pulsating light source. For example, in U.S. Pat. No. 4,021,102 issued to Iizuka on May 3, 1977, a refractometer is shown including a pair of infra-red light sources which are alternately flickered. The light beams generated by the light sources are passed through a vertical slit which is movable to permit focus of the slit image on the retina of the patient's eye. The slit image on the retina is reflected via a prism to a pair of photodetectors. The difference between the signals detected by the pair of photodetectors is then measured and, if no difference is detected, the visual acuity of the patient's eye is normal. However, if the eye is myopic or hyperopic, the slit image is not properly focused on the retina and the reflected slit image detected by the photodetectors results in a DC difference which actuates a compensating lens system to automatically correct the focus of the eye.

Finally, a number of other prior art patents show refractometers which use a primary target pattern for measuring the visual acuity of the patient's eyes. Some of these prior art patients use flashing or pulsating sources of light such as U.S. Pat. No. 3,843,240 issued to Cornsweet on Oct. 22, 1974. Others of these prior art refractometers and other visual acuity devices use a target pattern which is illuminated by a light source which is periodically interrupted by rotating drums or reticles. For example, the Munnerly patent cited above shows a rotating drum or reticle for interrupting the beam of light directed through the target pattern to the patient's eye.

Although all the above prior art devices objectively measure the acuity of a patient's eyes, and provide accurate and automatic arrangements for measuring visual acuity, these devices are not practical for mass vision testing because they require trained specialists for operation, they are large and complex mechanisms, and they are prohibitively expensive. Furthermore, these prior art devices generally are not flexible enough to measure both near and far visual acuity.

SUMMARY OF THE INVENTION

The primary object of the present invention is to provide a visual acuity device which overcomes the above mentioned disadvantages of the prior art visual acuity devices and is both simple to operate and inexpensive. In particular, it is an object of the present invention to eliminate the complex lens systems, the complicated mechanics, the extensive electronics and the photomultipliers of the prior art visual acuity devices.

It is a further object of the present invention to provide a visual acuity device which is accurate, easy to use, compact, portable, and highly reliable. In this regard, operation by trained specialists is not required because the simple design of the present invention makes operation with accurate results available almost to any person. In addition, large pedestal type devices are replaced by the easily portable visual acuity device of the present invention. These features, together with the low cost of the visual acuity device of the present invention, make mass vision examination of preschool children practical.

It is also an object of the present invention to provide a visual acuity device for measuring both far and near visual acuity. In this regard, it is an object of the present invention to provide different types of read-out devices for indicating near and far visual acuity including continuous read-out of visual acuity in either digital or analog form.

It is a further object of the present invention to provide a visual acuity device that simultaneously detects the in-focus signal reflected from the patient's eye and cancels the out-of-focus signal or glare. Furthermore, it is an object of the present invention to provide a visual acuity device which uses a primary pattern having a relatively large area so that the total light directed on the patient's eye is much greater and, as a result, a stronger reflected signal is generated for easier detection.

The present invention is a visual acuity device for measuring the visual acuity of a patient's eye by projecting an image on the eye which corresponds to a primary pattern; the focus of the image on the patient's eye is then detected. The visual acuity of the eye corresponds to the line spread of the reflected image of the primary pattern. A discussion of the correspondence between line spread and visual acuity can be found in the technical article "Optical Quality of the Human Eye" by F. W. Cambell and R. W. Gubisch, Journal of Physiology, 186: pp. 558–578 (1966). Although correspondence between line spread and visual acuity has been known for some time, the present invention is directed to a unique arrangement for determining visual acuity by measuring line spread.

In particular, the visual acuity device of the present invention is a combination of an optical system for projecting an image on the patient's eye and receiving the reflected image and a signal detection circuit for generating a signal in response to the reflected image which corresponds to the visual acuity of the eye. A light source is provided for producing a pulsating beam of light which is transmitted to the patient's eye by the optical system. The optical system includes a primary pattern which is positioned near the light source in the direct optical path of the beam of light. The primary pattern is mounted in a fixed position and it has a pattern consisting of a plurality of interleaved transparent and non-transparent portions. An image of the primary pattern is reflected by the retina of the patient's eye and transmitted by the optical system to a pair of analyzer or secondary patterns which are also mounted in a fixed position. One of the analyzer or secondary patterns has a pattern which substantially corresponds to the pattern of the primary pattern and the other has a pattern which is the negative or opposite of the pattern of the primary pattern. In other words, one of the analyzer or secondary patterns admits the in-focus image of the primary pattern reflected from the patient's eye and other analyzer or secondary pattern blocks the in-focus reflected image. A photoelectric device is associated with each of the analyzer or secondary patterns for detecting the pulsating light reflected from the patient's eye through each of the analyzer patterns. The signal detection circuit is connected to these photoelectric devices to measure the difference between the electric signals generated by these photoelectric devices to thereby cancel the out-of-focus glare in the reflected image. The resulting difference signal is then used in any one of a number of ways to determine the visual acuity of the patient's eye.

In one embodiment, the visual acuity of the patient's eye is measured by directly measuring the differennce signal with a peak hold detector and a DC voltmeter. In more sophisticated embodiments, visual acuity can be measured by using digital pulse techniques by connecting the peak hold detector to an encoder/decoder circuit which drives an LED display to indicate the visual acuity. Timing signals also can be provided to synchronize the operation of the signal detection circuit for measuring visual acuity with the pulsating beam of light. In addition, visual acuity can be measured by adjustment of a lens set, a compensating lens, etc. to focus the target image on the retina of the eye together with observation of the difference signal generated by the signal detection circuit. In this latter case, when the eye reflects an in-focus image, the visual acuity can be determined by the position of the compensating lens, the power of the particular lens of a lens set, etc. All these variations of the electronic arrangement can be used in the present invention to simply and easily measure the visual acuity of the patient's eye.

Finally, the visual acuity device of the present invention also can be used to measure far visual acuity. A pulsating infrared light source together with a collimating lens prevents accomodation by generating parallel-infrared light rays to make the primary fixation pattern appear at optical infinity. The reflected image is then transmitted through a compensating lens and the secondary patterns for detection by the photoelectric devices. The electronic circuit connected to the photoelectric devices then generates a signal which is used to indicate the far visual acuity of the eye.

DETAILED DESCRIPTION OF THE DRAWINGS

Figure 1:
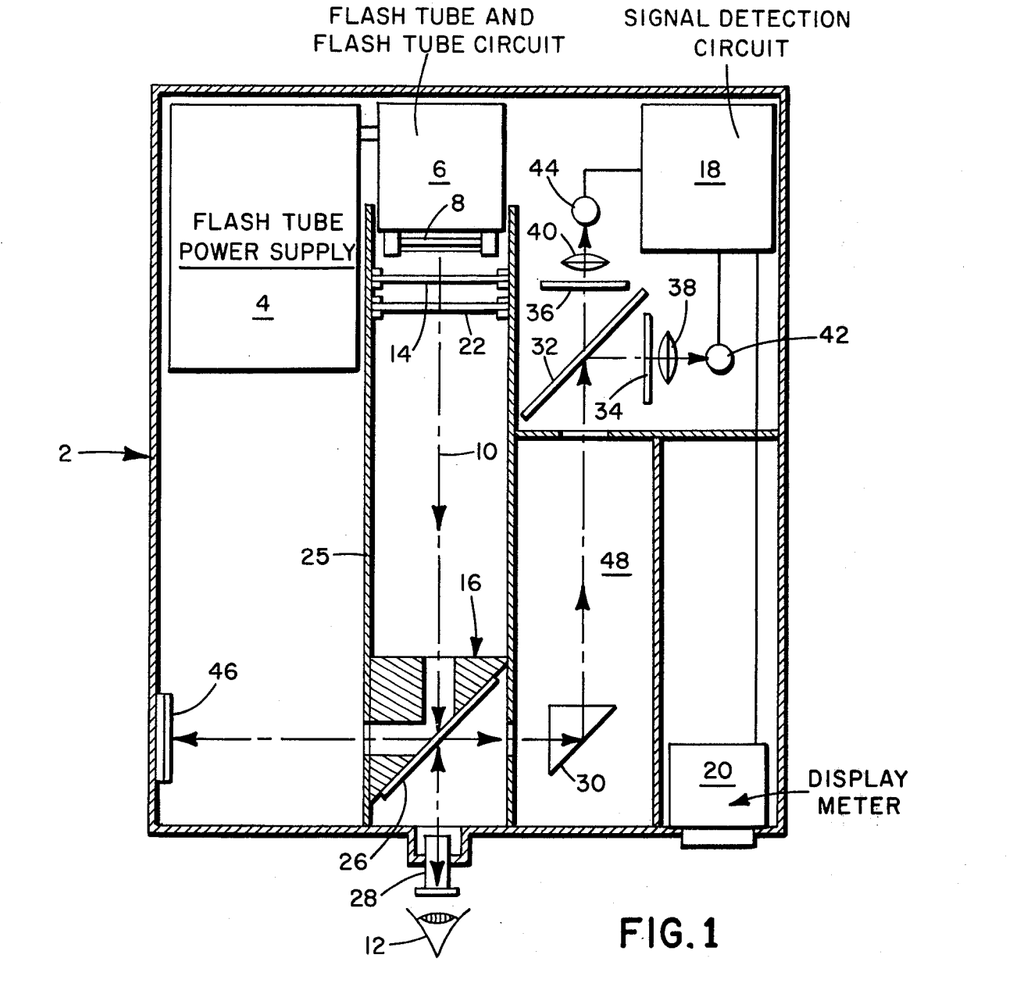
FIG. 1 is a diagram showing a top view of the arrangement of the housing of the visual acuity device.

The housing 2 of the pulse pattern visual acuity device of the present invention is shown in FIG. 1. The housing 2 contains a power supply 4 for supplying power to the flash tube circuit 6 which contains a flash tube 8 as illustrated in greater detail in FIGS. 2 and 3. The flash tube circuit 4 and the flash tube 6 together form a pulsating light source which generates a pulsating beam of light 10 directed to the eye of a patient under examination. The pulsating beam of light 10 is transmitted to the eye 12 by an optical system 16. The optical system 16 also transmits a reflected image from the eye 12 to a signal detection circuit 18 which is connected to a display device 20, such as a display meter, to display the visual acuity measurement of the patient's eye.

Figure 2:
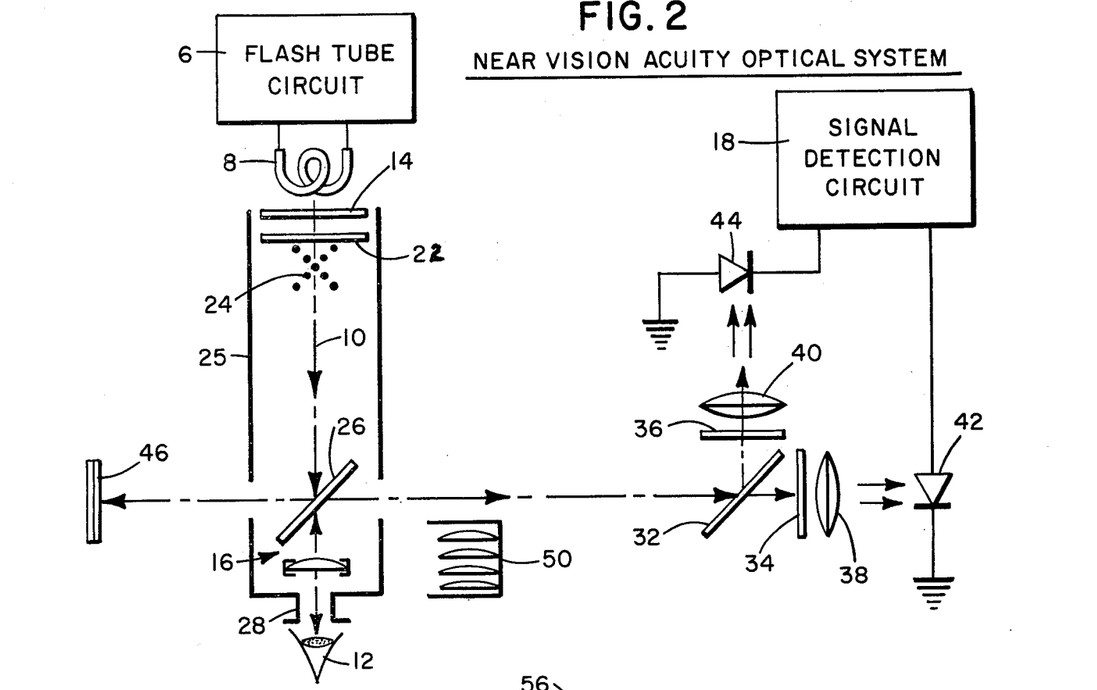
FIG. 2 is a diagram showing the optical system for one embodiment of a near visual acuity device of FIG. 1.
Figure 3:
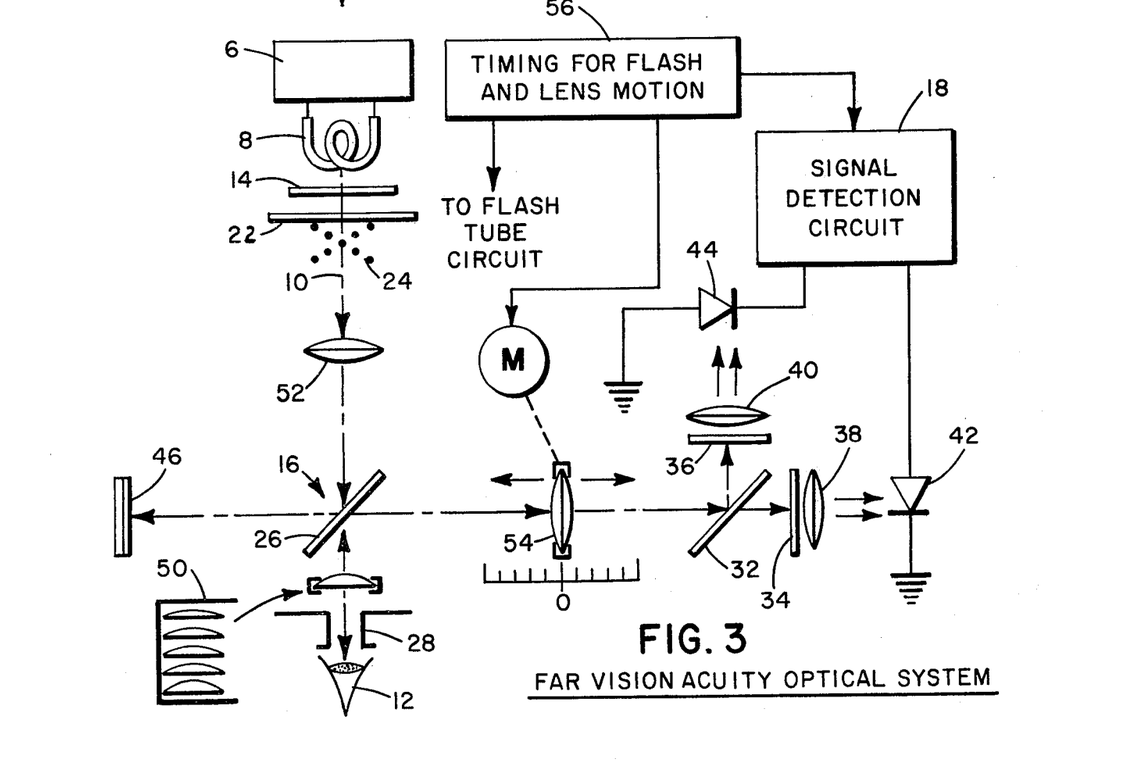
FIG. 3 is a diagram showing the optical system for one embodiment of a far visual acuity device according to the present invention.
Figure 7A:
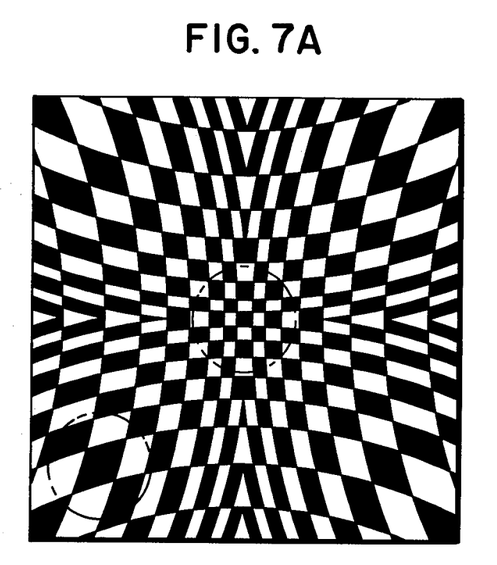
FIG. 7A shows an equal area pattern for the primary pattern.

Although the basic elements of the optical system are shown in the housing 2 of FIG. 1, additional details of the optical system 16 for a near vision visual acuity device are shown in FIG. 2 and additional details for a far vision visual acuity device are shown in FIG. 3. A primary pattern 22 is positioned adjacent the flash tube 8 so that the pulsating beam of light 10 passes along channel 25 from the flash tube 8 through the primary pattern 22 to the patient's eye 12. As a result, the retina of the patient's eye 12 reflects an image of the primary pattern 22 in a manner generally known in the art. Any pattern may be used as the primary pattern 22. However, it should be noted that the measurement of visual acuity according to the present invention depends on the analysis of the line spread of the reflected image of the primary pattern from the retina of the eye 12. The relationship between line spread and visual acuity is discussed in the article entitled "Optical Quality of the Human Eye" by F. W. Cambell and R. W. Gubisch, Journal of Physiology 186: pp. 558-578, 1966. Since the measurement of visual acuity according to the present invention is a function of line spread, the size and layout of the primary pattern 22 must be taken into account in adjusting the visual acuity device to measure visual acuity. An example of a radial pattern 22 is shown in FIG. 5A whereas an example of an equal area primary pattern 22 is shown in FIG. 7A. In addition, a fixation cross 24 is positioned in front of the primary pattern 22 to provide a fixation point for the eye 12 of the patient. The fixation cross 24, which is generally known in the art, may consist of a pattern of alternating red/green/-blue/yellow fixation crosses.

The flash tube 8 and the flash tube circuit 6 generate a light pulse at the rate of approximately 50 Hz or approximately one per second. These light pulses form the pulsating beam of light 10. A pulsating beam of light 10 is used to dramatically increase the peak power more than 1000 times without an increase in average power. By increasing peak power, relatively insensitive, but very simple and very low cost, semiconductor photodiodes 42 and 44 can be used as described in further detail below. The use of this pulsating beam of light 10 results in considerable improvement in the signal to noise ratio of the visual acuity device. In addition, the pulsating beam of light 10 preferably is infrared light. An infrared filter 14 is positioned between the flash tube 8 and the primary pattern 22 as shown in FIGS. 1-3. The use of infrared light prevents photophobia since the pulsating beam of light 10 is more than 1000 times brighter than a continuous light source of the same average power. Pulsed visible light would blind the eye whereas infrared light is invisible to the eye. In addition, the low level of visible light, the pupil expands to enable a stronger reflected signal, that is, more light enters the eye and more light is reflected. A larger, normal size pupil results in visual acuity measurements which are more accurate. In measuring far vision visual acuity as shown in FIG. 3, an infrared pulsating beam of light 10 is used as well as a luminous fixation crosspoint 24 in a darkened field so that the eye is unable to focus and the lens of the eye is relaxed in a normal, far vision state. Accomodation of the eye is avoided by using a luminous fixation crosspoint 24 which appears at optical infinity.

It should be noted that the internal dimensions of the housing 2 of the visual acuity device, are small. The distance for the eyepiece 28 to the primary pattern 22 is only 14 inches. For measurement of near vision with the visual acuity device the positioning of the primary pattern 22 at a distance of 14 inches forces near vision accomodation. The distance of 14 inches is the normal reading distance at which near vision is measured. On the other hand, for measurement of far vision, several modifications must be made in the apparatus as illustrated in FIG. 3 and described in further detail below.

Figure 6:
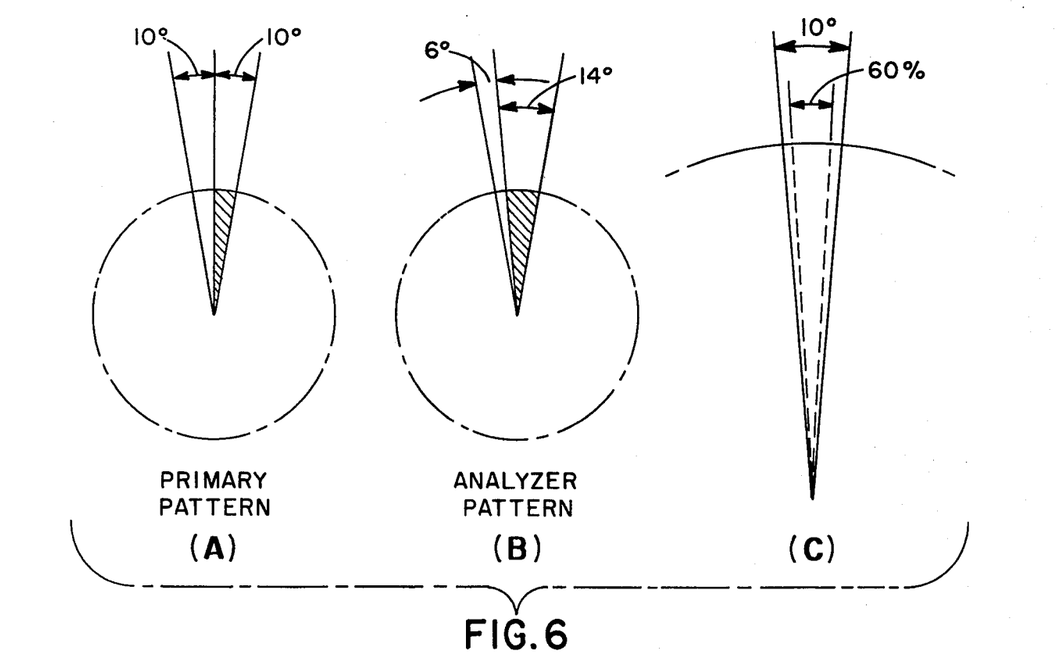
FIGS. 6A-C show a modified radial pattern for the primary and analyzer patterns.

The pulsating beam of light 10 generated by the flash tube 8 passes through the infrared filter 14, the primary pattern 22 and the fixation cross 24 to a beam splitter 26. The primary function of the beam splitter 26 is to direct the reflected image of the primary pattern on the retina of the eye 12 along a different path from the pulsating beam of light 10. An anti-reflective device or glare stop 46 is provided adjacent the beam splitter 26 to reduce the amount of glare generated in the housing 2 by the reflection of the pulsating beam of light 10 as well as the reflected image from the retina of the patient's eye 12. The reflected image of the primary pattern 22 from the retina of the eye 12 is directed to the beam splitter 26 as shown in FIGS. 1-3. The beam splitter 26 splits the reflected light from the eye 12 and directs the reflected light toward the prism 30 which is positioned in the reflection channel 48. The prism 30 redirects the reflected light along the reflection channel 48, thereby enhancing the compactness of the housing 2, toward the beam splitter 32. The beam splitter 32 again splits or evenly divides the reflected light to each of a pair of analyzer or secondary patterns 34 and 36. One of the analyzer patterns is positive or admits the in-focus image reflected from the retina of the eye 12 while the other analyzer pattern is negative and blocks the infocus image reflected by the retina. In other words, the pattern of one of the analyzer patterns is essentially the same as the primary pattern 22 while the other is the opposite or the negative of the primary pattern 22. For example, in FIG. 6B, one of the radials of a radial analyzer pattern is shown which is substantially the same as the primary pattern shown in FIG. 6A. The other analyzer pattern associated with the analyzer pattern in FIG. 6B is the opposite of or the negative of the analyzer pattern in FIG. 6B.

As mentioned above, in the pulse pattern visual acuity device, visual acuity and line spread are determined by the size of the figures in the primary pattern and the percent of the primary pattern that is admitted or blocked by the analyzer patterns. First, small figures are used to measure high visual acuity and large figures are used to measure low visual acuity. For example, a pattern with tiny 0.5 millimeter squares (checkerboard, 50 percent transparent and 50 percent opaque) would produce a signal only with high visual acuity. Large 5 millimeter squares would produce a signal either with high or low visual acuity, and a slightly higher signal with higher visual acuity.

Secondly, if the analyzer pattern have openings less than 50 percent, more line spread (more blur) is required to reduce the analyzer signal. Referring to FIG. 6A, one of the radials of the primary pattern 22 is shown having successive opaque and transparent portions at 10 degree intervals. In practice, the primary pattern is not quite 50/50 because refraction at the edges of the pattern and at the pupil causes a small amount of line spread. So the primary pattern 22 in FIG. 6A actually would appear to be 9.5 degrees open and 10.5 degrees closed. Referring to the analyzer pattern of FIG. 6B, in order to make alignment easier with the primary pattern, the analyzer patterns for the primary pattern in FIG. 6A are 6 degrees open and 14 degrees closed. FIG. 6C shows the changes in the required line spread in relation to the radial distance. At the outer region of the pattern, larger line spread is required whereas near the center of the pattern small line spread affects the resulting signal. This is further illustrated in FIGS. 5A-5C where the line spread of a radial pattern for different visual acuity measurements is shown. FIG. 5A shows line spread for normal vision; FIG. 5B shows line spread for 20/200 vision in which the center portion of the pattern is blurred and the line spread of the outer portion of the pattern is observable; and FIG. 5C shows line spread for 20/400 vision in which a large portion of the central region of the pattern is blurred and only the outermost region of the pattern is observable. In other words, FIGS. 5A-C essentially show the image of the primary pattern reflected by the retina of the patient's eye 12. In accordance with the present invention, these different reflected images are used to generate electrical signals which determine visual acuity.

Differences in visual acuity measurements can be more easily differentiated with finer radial patterns such as a radial pattern which is 5 degrees open and 5 degrees closed because the figures are smaller. These finer radial patterns operate to clearly differentiate small differences in order to detect amblyopia or lazy eye, which if not corrected at an early age can lead to blindness. By using the finer 5 degree pattern, however, the overall measurement range of visual acuity is reduced. For a wide range of visual acuity measurements, there should be both small and large figures, hence an equal area pattern such as shown in FIG. 7A is used. However, it is noted that the same desired result can be achieved with radial patterns by adjusting the size of the openings of the analyzer patterns, that is, providing analyzer patterns having openings less than 50 percent requires more line spread in order to reduce the analyzer signal. In summary, the primary pattern 22 is either positive or negative (as in a transparency with opaque emulsion) and one of the analyzer patterns is negative and the other one is positive. The primary pattern 22 could be asymmetrical or symmetrical, but in either event, the analyzer patterns 34 and 36 must be positive-negative mirror images of each other.

Returning now to FIGS. 1-3, the two fixed analyzer or secondary patterns 34 and 36 are essential to the operation of the visual acuity device of the present invention. These analyzer patterns 32 and 36 are used to detect the contrast, that is, light and dark areas of the primary pattern as seen by the eye 12 and reflected by the retina. One of these analyzer patterns admits the "light" areas and the second analyzer pattern blocks the "light" areas of the primary pattern. These patterns 34 and 36, like the primary pattern 22, can be symmetric or asymmetric. Even an ordinary photographic transparency of a street scene could be used to make the patterns as long as the primary pattern is either positive or negative and the analyzer patterns consist of one negative and one positive pattern. For simplicity, however, a symmetrical pattern is preferred.

A pair of lenses 38 and 40 are positioned behind the analyzer patterns 34 and 36, respectively. These lenses concentrate the reflected light passing through the analyzer patterns 34 and 36 and direct the reflected light to a pair of photodiodes 42 and 44, respectively. These photodiodes 42 and 44 are electrically connected to the signal detection circuit 18. The analyzer patterns 34 and 36 pass the reflected image of the retina of the eye 12 and the signal detection circuit detects the electrical difference signal in the two photodiodes 42 and 44. Essentially, this combination of positive and negative analyzer patterns 34 and 36 together with the detection of the different signal by the signal detection circuit 18 eliminates or cancels the glare in the optical system so that visual acuity can be accurately measured. The signal detection signal 18 basically comprises a differential amplifier, a filter or slicer, and a display circuit including a display device. Various modifications can be made in this signal detection circuit to achieve automatic operation, etc. as described in further detail below.

The optical system 16 for the near vision visual acuity device is shown in detail in FIG. 2. In measuring near vision line spread, the overall optics provide a type of autocollimation because, when the primary pattern 22 is in focus at the retina of the eye 12, the eye reflects the in-focus image to the analyzer patterns 34 and 36. It should also be noted that for near vision measurement, d1=d2 and d1+d3 (d1 is 20 to 26, d2 is 26 to 34 or 36, and d3 is 26 to 12)=14 inches, which is the standard reading distance. Several different techniques can be used for determining the near vision visual acuity. First of all, a trial lens set 50 may be used in which the lenses are varied in order to obtain the maximum signal at the display meter 20 through the signal detection circuit 18. The visual acuity then would be determined by the particular lens used to achieve the maximum signal. The lens set 50 could be constructed of individual lenses in a revolving turret, a single compensating lens moved to and fro or a combination of two or more lenses moved closer/farther apart. When a lens set 50 is used, the visual acuity device functions as an automatic refractometer. Alternatively, visual acuity can be measured by changing the size of the primary pattern 22 where the pattern size itself is related to visual acuity. Finally, the signal strength of the signal generated by the signal detection circuit 18 corresponds to line spread which in turn corresponds to visual acuity. In other words, visual acuity is proportional to the signal strength of the signal detected by the signal detection circuit 18 and displayed on the display device 20. The display device 20 can be calibrated to indicate visual acuity. This technique can also be combined with the use of the trial lens 50 by observing whether the signal strength increases or decreases when a plus or minus trial lens is used thereby indicating diopters. That is, for plus or minus diopter determination, a small plus or minus diopter lens flips into the visual path. By observing whether the signal increases, the plus or minus diopter determination can be made. As described in further detail below, the insertion of different lenses into the visual path can be performed automatically using a simple logic circuit with an output to the display device 20 which may be an LED indicator and by pushing a button on a panel to cause the lens to be flipped into place.

Figure 4:
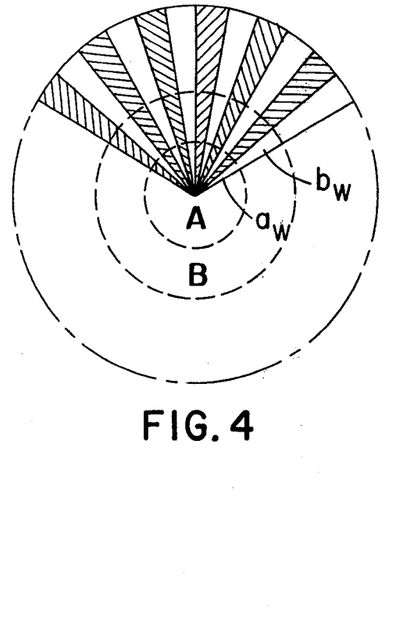
FIG. 4 shows a portion of a radial pattern for the primary pattern.
Figure 5:
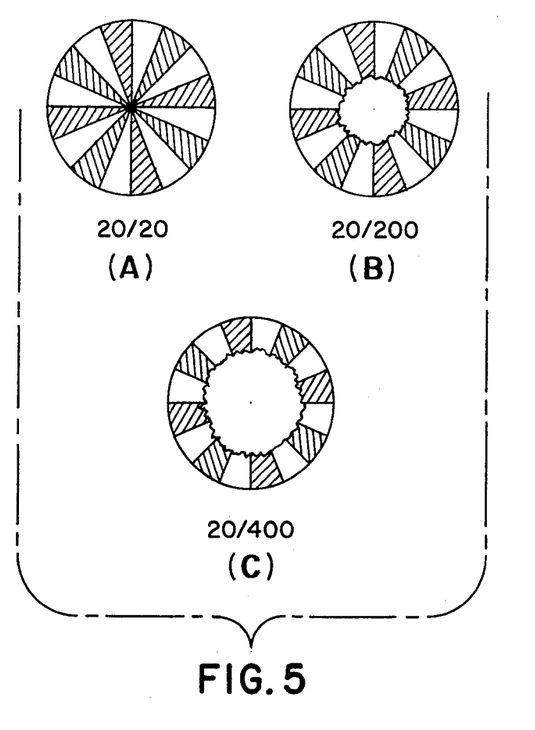
FIGS. 5A-C show reflected images of the radial pattern of FIGS. 4 demonstrating differences in line spread for 20/20, 20/200 and 20/400 vision, respectively.

When a radial primary portion such as shown in FIG. 4 is used, signal strength is proportional to the visual acuity. In this radial pattern, closed and open portions occur at 10 degree intervals. Since the actual distance between the opaque sections of the radial pattern in FIG. 4 is different for area A and area B, the line spread measurement or signal strength will vary as a function of visual acuity. For example, as shown in FIG. 5, line spread is blurred in the central portion of the radial pattern for 20/200 vision and it is even further blurred for 20/400 vision.

Figure 7B:
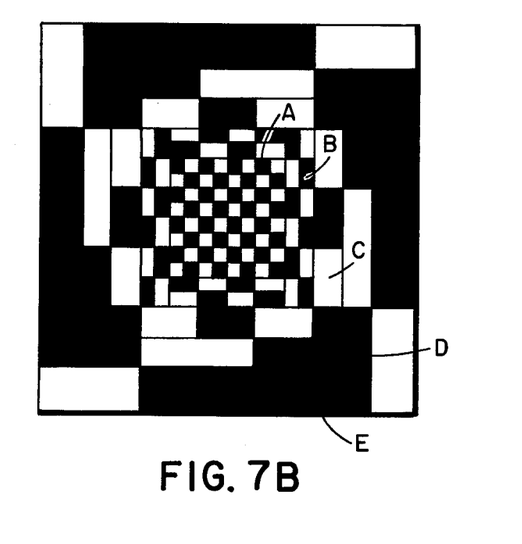
FIG. 7B is a diagram illustrating the equal areas of the equal area pattern of FIG. 7A.
Figure 7C:
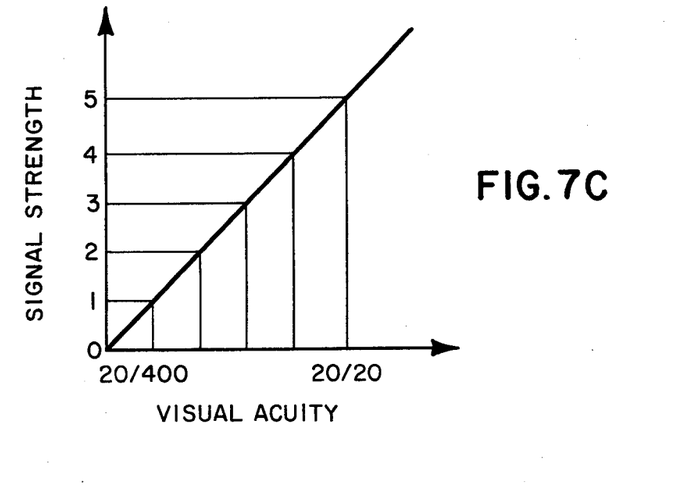
FIG. 7C shows a linear graph of visual acuity versus signal strength for the equal area pattern.

It is also possible to construct a primary pattern 22 in which visual acuity is linearly related to the signal strength or line spread. The line pattern 22 shown in FIG. 7A is an equal area pattern in which area A of the pattern in FIG. 7A corresponds to 20/20 vision and consists of one-fifth the total area; area B corresponds to 20/60 vision and consists of one-fifth the total area; area B corresponds to 20/60 vision and also is one-fifth the total area; each of areas C, D and E is one-fifth the total area and correspond to vision measurement up to 20/400. These respective areas are shown diagrammatically in FIG. 7B as being equal to each other. The equal areas pattern of FIG. 7A is geometrically expanded pattern in which areas A—E are continuous to obtain proportionally linear measurements from 20/20 to 20/400. Thus, for this equal area primary pattern 22, signal strength is linearly related to visual acuity as illustrated by the graph in FIG. 7C.

Turning now to FIG. 3, a far vision visual acuity device is shown therein in which a collimating lens 52 is inserted in the optical path of the pulsating beam of light 10. The collimating lens 52 provides parallel infrared rays in the pulsating light beam 10 so that the fixed pattern appears at optical infinity. In addition, an adjustable compensating lens 54 is inserted in the optical path of the reflected image between the beam splitters 26 and 32. The compensating lens 52 makes the distance between the beam splitters 26 and 32 appear to be at optical infinity so that an in-focus reflected image from the retina of the eye would be sharply reproduced at the analyzer or secondary patterns 34 and 36. Finally, it is noted that the lens of the eye 12 must be unaccomodated for measurement of far visual acuity. Therefore, the pulsating beam of light 10 must be infrared and a luminous fixation point must be used to prevent accomodation. If far vision visual acuity is not normal, a sharply reproduced reflected image of the primary pattern 22 can be obtained at the analyzer patterns 34 and 36 by either adjustment of the lens set 50 or by adjustment of the compensating lens 54. The adjustment of the lens set 50 or the adjustable compensating lens 54 produces a maximum signal on the display device 20 through the signal detection circuit 18. This adjustment corresponds to the patient's visual acuity. In addition, visual acuity can be obtained by a direct measurement of the signal strength of the signal generated by the signal detection circuit 18. Also as shown in FIG. 3, a timing circuit 56 can be provided for controlling the signal detection circuit 18 as well as the flash tube circuit 6. This timing circuit 56 can also be used to automatically drive or move the adjustable compensating lens 54.

Figures 8, 9:
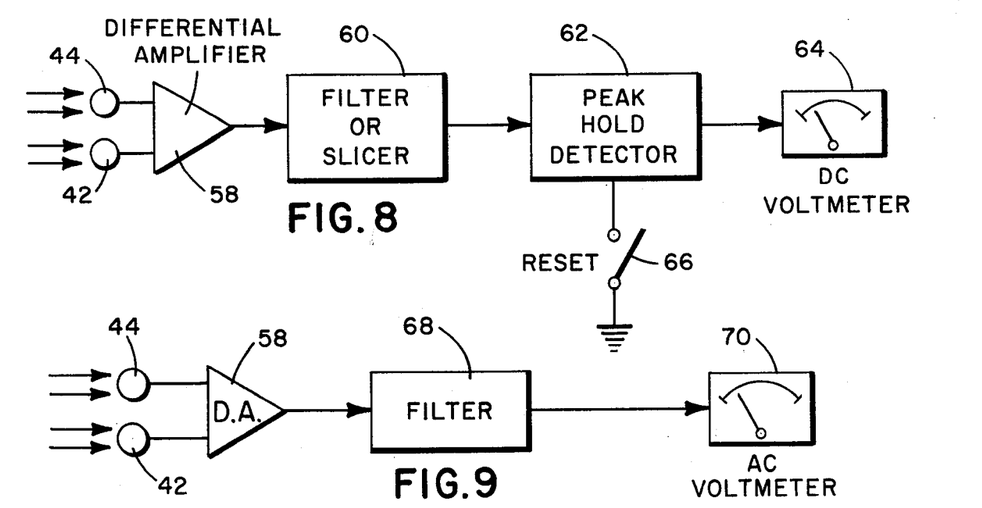
FIG. 8 shows a first embodiment of the signal detection circuit of FIGS. 2 and 3 having a DC voltmeter output.
FIG. 9 shows another embodiment of the signal detection circuit of FIGS. 2 and 3 having an AC voltmeter output.

A basic signal detection circuit 18 is shown in FIG. 8. The differential amplifier 58 is connected to the photodiodes 42 and 44. Since one of these photodiodes 42 and 44 detects the reflected image which is admitted by one of the analyzer or secondary patterns 34 and 36 and the other photodiode detects the blocked reflected image, the difference signal generated by the differential amplifier 58 balances out or cancels glare and an in-focus signal appears at the output of the differential amplifier 58. Although it is possible to use a filter 68 and an AC voltmeter 70 as shown in FIG. 9 to measure the signal strength of the signal generated by the differential amplifier 58, in general, this is not a practical alternative because of the small amount of light reflected by the retina and the low frequency of the pulsating beam of light 10. Thus, as illustrated in FIG. 8, the signal generated by the differential amplifier 58 is provided to a filter or slicer 60. The filter 60 reduces spectral noise of the type 1/f by the square root of f. For example, if flash frequency is 1/2000th second and the filter 60 is a 1000 Hz filter, the signal to noise ratio can be improved by the square root of 1000. The significance of improving the signal-to-noise ratio means that either the power of the pulsating beam of light 10 can be reduced or the pulse rate can be increased for the same unfiltered signal-to-noise ratio. The output of the filter 60 then is supplied to the peak hold detector 62. The peak hold detector 62 holds the peakk signal generated by the differential amplifier 58. As a result, despite changes in accomodation during examination of the patient's eye 12 as well as the use of a pulsating beam of light 10, a continuous output signal can be obtained for the DC voltmeter 64. The DC voltmeter 64 can be calibrated to indicate the signal strength of the signal detected by the differential amplifier 58 so that visual acuity can be determined by any one of the methods described above. Finally, the peak hold detector 62 can be reset by actuation of the reset switch 66.

It should be noted that the photodiodes 42 and 44 should receive equal amounts of light from the beam splitter 32 in order to properly measure visual acuity. Any imbalance in the amount of light detected by the photodiodes 42 and 44 can be corrected by adjusting the common mode rejection resistor of the differential amplifier 58. This differential amplifier 58 is a balanced amplifier since the signal common to the inputs of the differential amplifier 58 can be balanced. A common mode rejection ratio of up to 120 db is possible by adjustment of the differential amplifier 58 and 85 db is easily obtainable.

Figure 10:
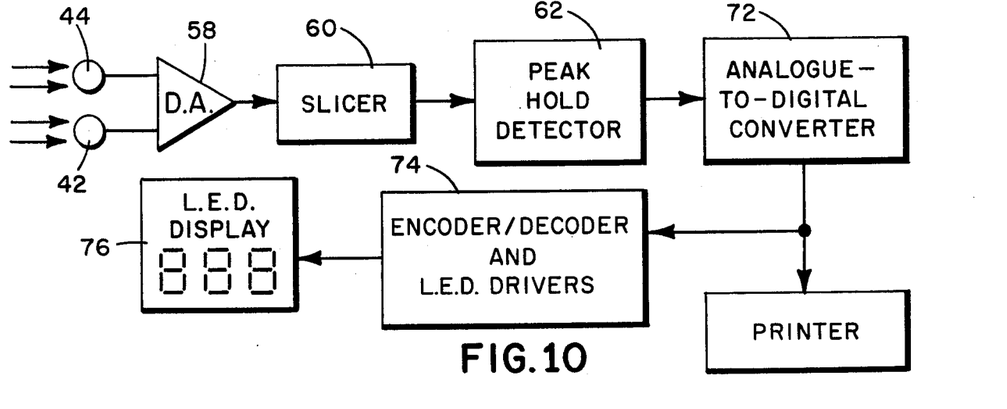
FIGS. 10 and 11 show additional embodiments of the signal detection circuit of FIGS. 2 and 3 having digital readouts.
Figure 11:
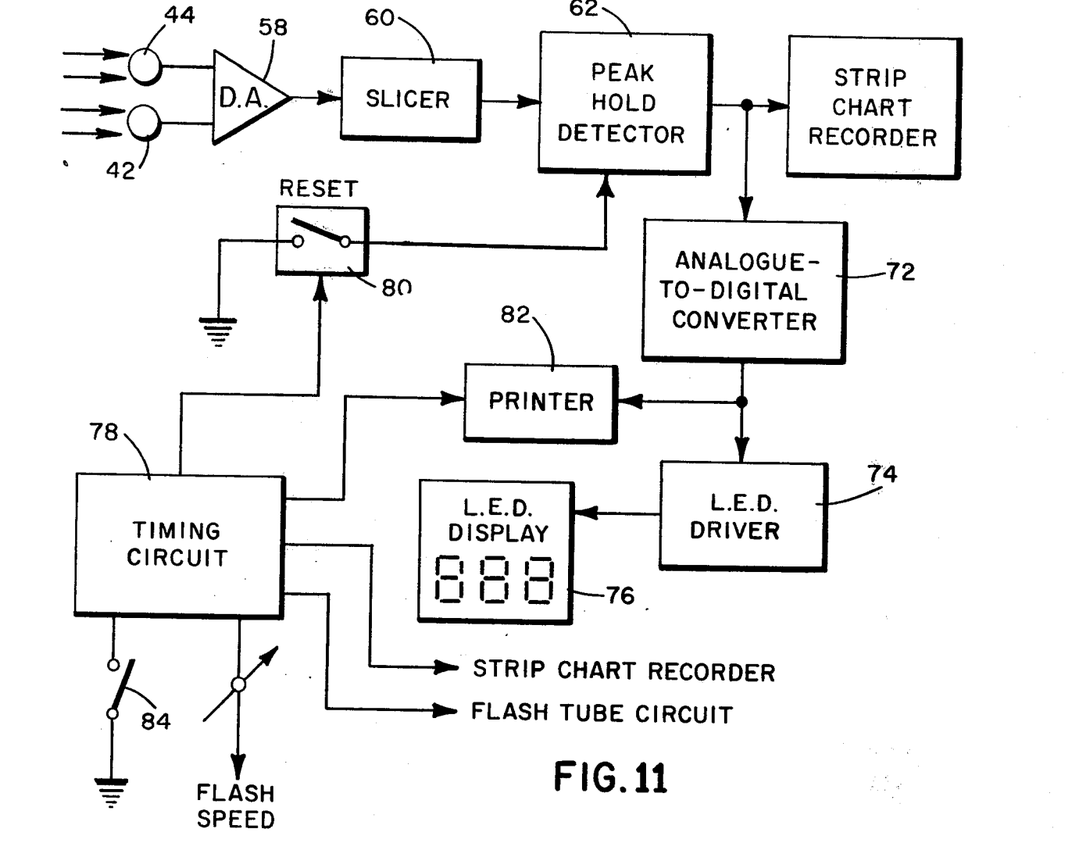

The visual acuity device of the present invention can be used to measure the visual acuity of the eye 12 using digital pulse techniques as illustrated in FIGS. 10 and 11. In FIG. 10, the output of the peak hold detector 62 is connected to an analog-to-digital converter 72 for converting the analog output of the peak hold detector 62 to a digital signal. The digital signal from the analog-to-digital converter 72 is encoded and decoded by the encoder/decoder 74. The encoder/decoder 74 also includes a driver circuit for driving the light emitting diodes of the LED display device 76. The LED display device 76 displays a digital read-out of the signal strength of the output signal of the differential amplifier 58. In addition, the output of the analog-to-digital converter 72 can be connected to a printer for printing the signal strength. A somewhat more sophisticated arrangement is shown in FIG. 11 wherein a timing circuit 78 is also employed for automatically resetting the peak hold detector 62 through the reset circuit 80. The timing circuit 78 also drives the printer 82 as well as a strip chart recorder and the flash tube circuit 6. An on-off switch 84 is provided for the timing circuit 78. The output at the peak hold detector is connected to the strip chart recorder so that the signal strength generated by the differential amplifier 58 can be recorded as a function of time.

Figure 12:
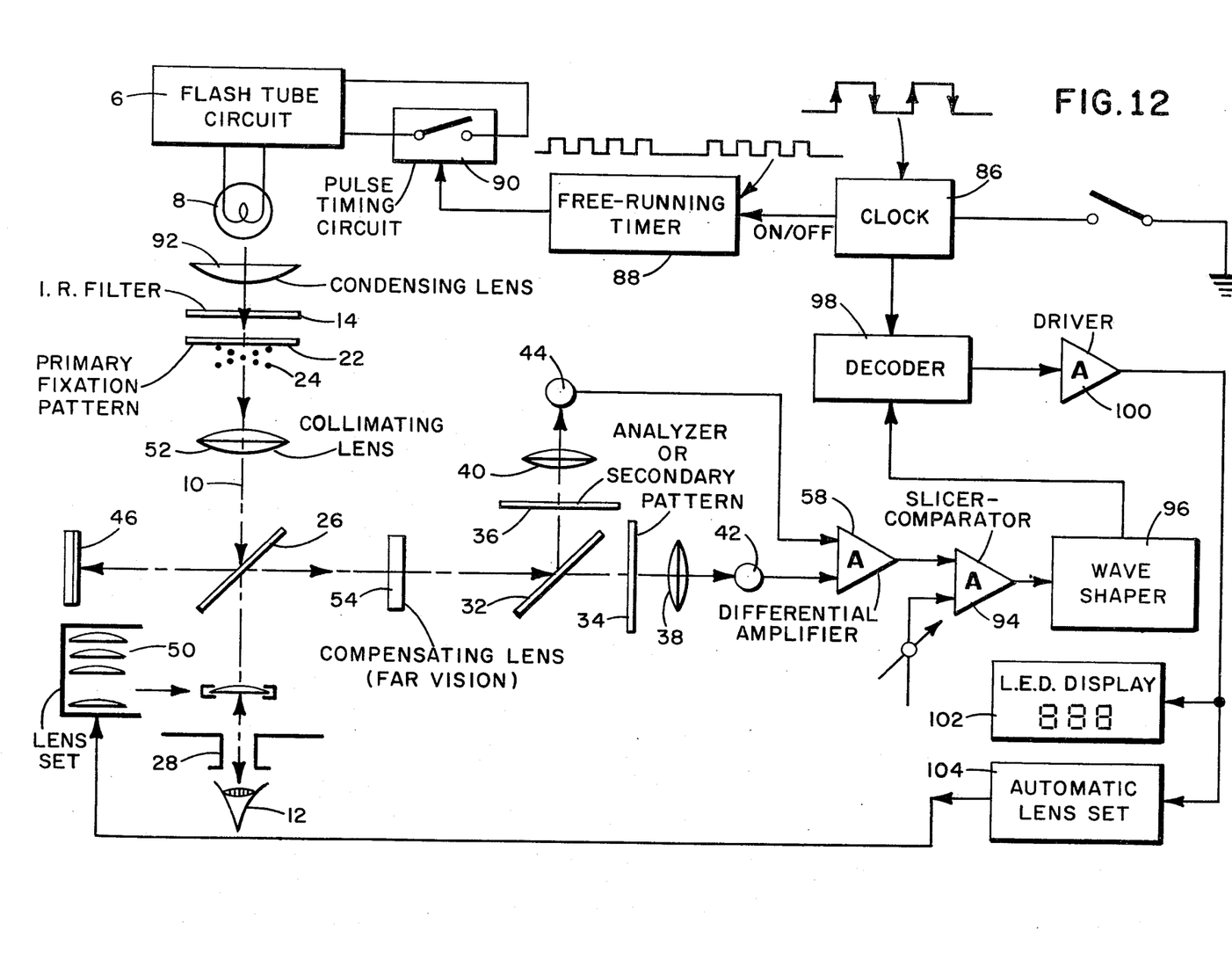
FIG. 12 shows a schematic diagram of another embodiment of the optical system and the signal detection circuit of the present invention.

A detailed embodiment of a digital pulse visual acuity device according to the present invention is shown in FIG. 12. A clock circuit 86 is provided for driving a free-running timer 88 which is connected to a pulse timing circuit 90. The combination of the clock 86, the free running timer 88 and the pulse timing circuit 90 drive the flash tube circuit 6 to enable the flash tube 8 to generate a pulsating beam of light 10. The pulsating beam of light 10 is condensed by condensing lens 92 and directed toward the eye 12 of the patient. An optional collimating lens 52 and an optional compensating lens 54 are provided for far vision visual acuity measurements. Thus, the visual acuity device of FIG. 12 can be used to measure both far and near vision visual acuity. The optical system 16 of the visual acuity device of FIG. 12 is the same as described above. In the signal detection circuit 18, the output of the differential amplifier 58 is provided to a comparator 98. The comparator is connected to a wave shaper 96 which provides a signal to the decoder 98. The decoder 98 also receives a clock signal from the clock 86. Thus, the operation of the decoder 98 is synchronized with the clock signals which are used to drive the flash tube circuit 6. The decoder 98 is connected to a driver 100 which is used to drive an LED display 102 for displaying the visual acuity of the patient's eye 12. The output of the driver 100 also drives an automatic lens set circuit 104 which automatically adjusts the lens set 50.

Figure 13:
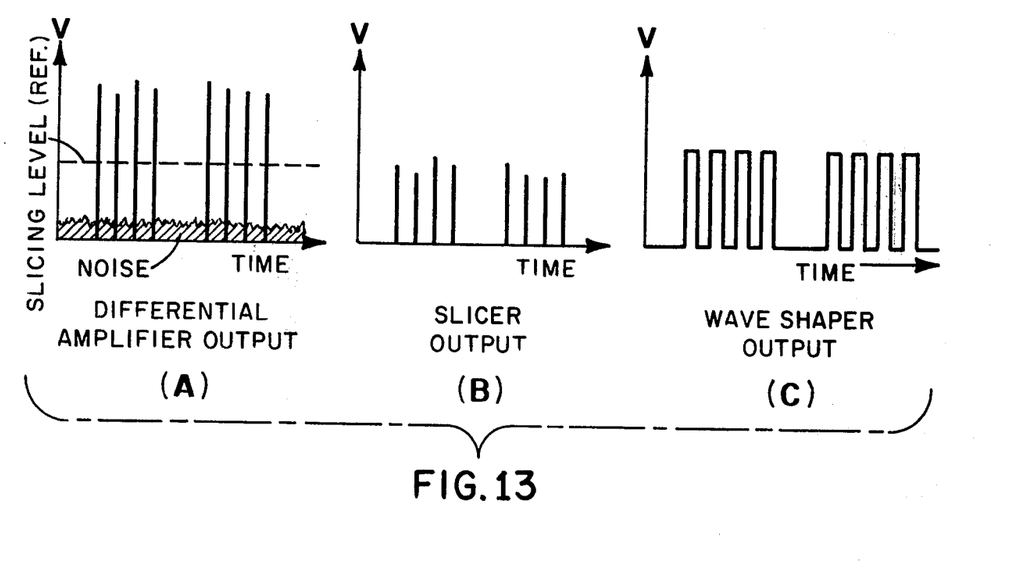
FIG. 13A-C show waveforms generated by the signal detection circuit of FIG. 12.

The visual acuity device of FIG. 12 achieves a very high signal-to-noise ratio by taking advantage of the fact that pulse signals require low average power yet have extremely high peak values. Peak to average ratios of 1000-1 are easily produced. As described previously, the reflected in-focus image from the retina of the eye 12 is detected by the difference in light levels between the two photodiodes 42 and 44. One of the analyzer patterns 34 and 36 admits the in-focus image and the other analyzer pattern blocks the in-focus image. The differential amplifier 58 amplifies the difference between the signals generated by the photodiodes 42 and 44 thereby cancelling the out-of-focus glare from the reflected image. The comparator circuit 94 further removes the glare signal as well as circuit noise. The output of the comparator 94 represents the significant difference between the signals generated by the photodiodes 42 and 44 which in turn represents an in-focus image. This output signal is shaped by the wave shaper 96 so that pulse signals can be detected by the decoder 98. Because the decoder 98 is responsive to the clock signal from the clock 86, the driver 100 produces output signals only when the appropriate series of pulses are received both from the photodiodes and from the clock 86. For example, where the clock 86 generates a series of four pulses or other binary-coded series of pulses as shown in FIG. 12, the signal detected by th photodiodes 42 and 44 can easily be distinguished from noise as illustrated in the graphs in FIGS. 13A–13C. The driver 100 is activated by the decoder 98 upon receipt of the series of four pulses from the clock 86 so that noise cannot produce an output signal.

Figure 16:
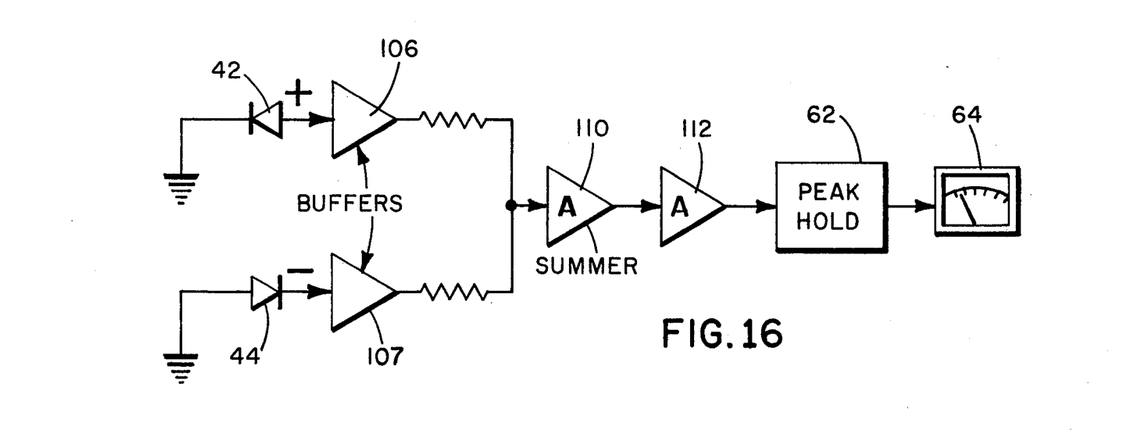
Figure 17:
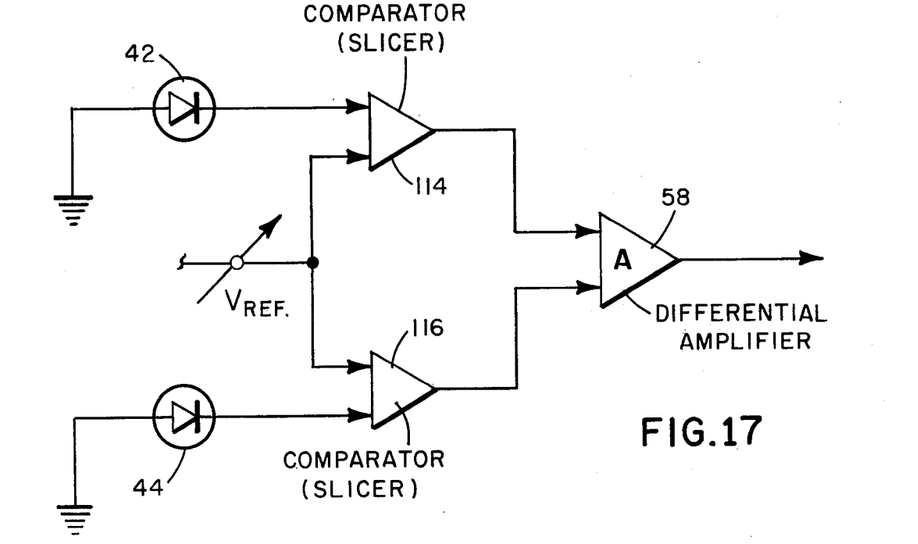

In FIGS. 16 and 17, further modifications of the signal detection circuits are shown. In FIG. 16, buffers 106 and 108 are connected to the photodiodes 42 and 44, respectively. The buffers 106 and 108 are buffers which match the high impedance of the photodiodes 42 and 44 to the low impedance of the summer 110. The outputs of the buffers 106 and 108 are combined in the summer 110 and provided to the amplifier 112. A combination of the buffers 106 and 108 and summer 110 detect the difference signal generated by the photodiodes 42 and 44. The output of the amplifier 112 is provided to peak hold detector 62 which is in turn connected to the meter 64. in FIG. 17, a pair of comparators 114 and 116 are connected to the photodiodes 42 and 44, respectively. A reference voltage is applied to each of the comparators 114 and 116. The comparators 114 and 116 are used to reduce the common mode signal from the photodiodes 42 and 44 to thereby reduce glare and generate an in-focus difference through the differential amplifier 58. This results in more efficient rejection of glare because the adjustment of the differential amplifier 58 is not as critical and the common mode difference signal ratio is generally reduced.

Figures 14, 15:
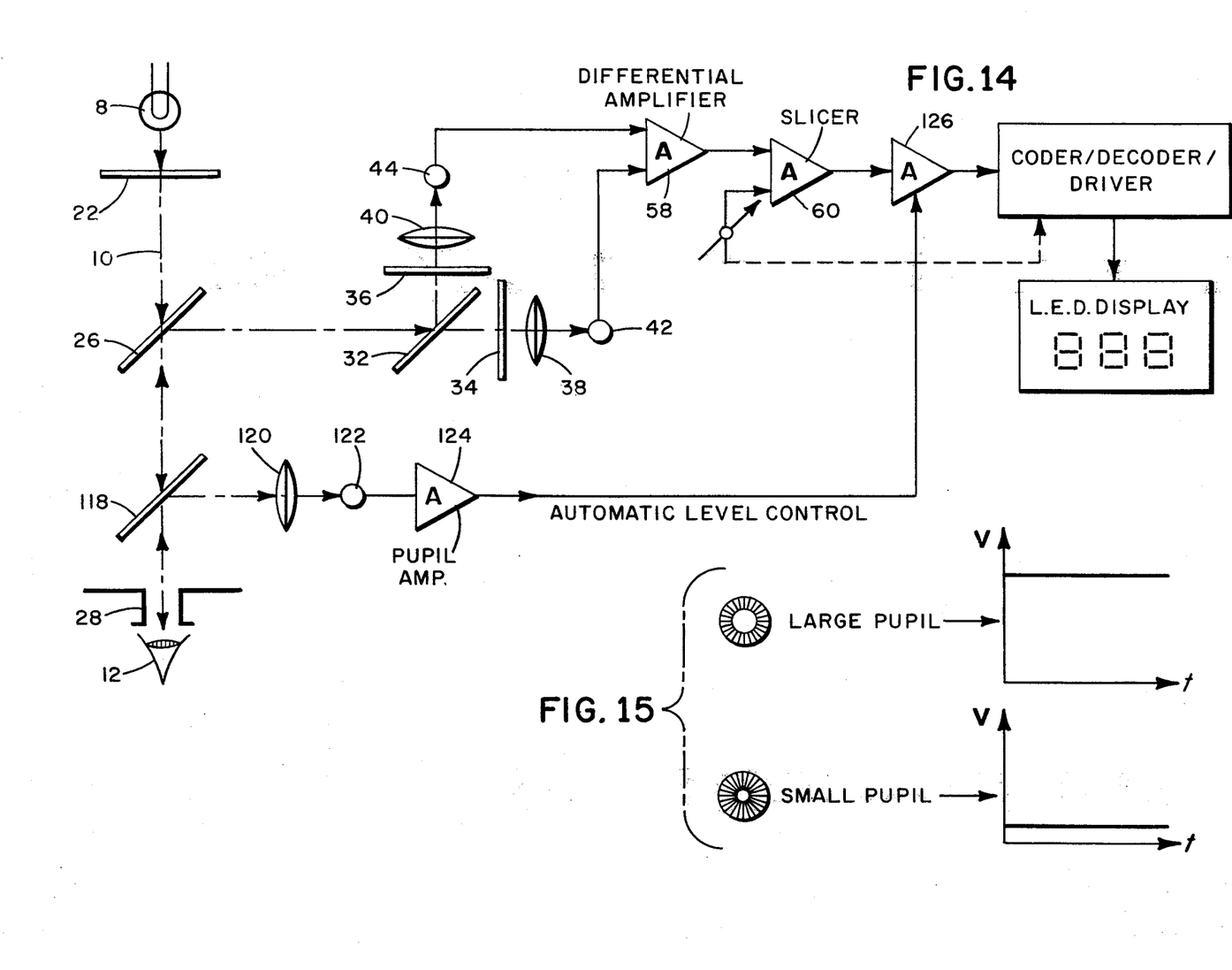
FIGS. 14-18 show additional modifications of the signal detection circuit of FIGS. 2 and 3.

Turning now to FIG. 14, a circuit arrangement is shown for eliminating the effect of pupil size on the signal strength detected by the signal detection circuit 18. The elimination of the effect of pupil size on signal strength increases the accuracy of the visual acuity measurement. This circuit includes a beam splitter 118 adjacent the eye 12 of the patient for directing the reflected image through a lens 120 to an infrared photodiode 122. The signal generated by the infrared photodiode 122 is supplied to an amplifier 124. The photodiode 122 and the amplifier 124 form an automatic level control feedback circuit which adjusts the amplification of the signal detection circuit 18 by adjusting the amplification of the voltage control amplifier 126. As a result, the visual acuity measurement of the visual acuity device is automatically adjusted in response to the pupil size detected by the photodiode 122. If a high output is detected by the photodiode 122, the amplification of the voltage controlled amplifier 126 is increased and, if a low output is detected by the photodiode 122, the amplification of the voltage controlled amplifier 126 is reduced. Thus, even with changes in pupil size, the measurement of visual acuity remains accurate. The effect of changes in pupil size for an in-focus image are illustrated by the graphs in FIG. 15 wherein a high voltage output from the signal detection circuitry is obtained for large pupil diameters and a low voltage output is obtained for small pupil diameters. Also, a fixed-diameter artificial pupil at the eyepiece can be used to eliminate pupil size effects.

Figure 18:
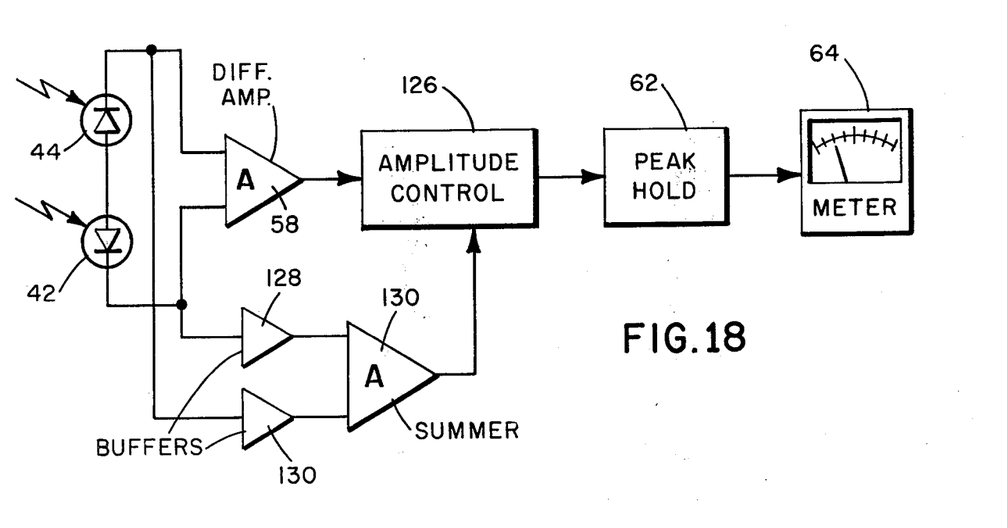

FIG. 18 shows a circuit equivalent to FIG. 14. This configuration eliminates the lens 120 and photodetector 122 to more simply suppress the effects of pupil size on signal strength.

The buffers 128 and 130 and the summer 132 restore the average glare level, which is masked by the positive and negative patterns of the in-focus signal. The amplitude control circuit 126 then functions as previously described. Also, note that this configuration uses two ungrounded photodetectors in a back-to-back arrangement.

Although illustrative embodiments of the invention have been described in detail with reference to the accompanying drawings, it is to be understood that the invention is not limited to those precise embodiments and that various changes and modifications may be effected therein by one skilled in the art without departing from the scope or spirit of the present invention.

I claim:

1. A visual acuity device for measuring the visual acuity of a patient's eye comprising:

light source means for generating a beam of light;
optical means for transmitting the beam of light from said light source means to the patient's eye and transmitting light reflected by the patient's eye, said optical means including a primary pattern adjacent said light source means in the optical path of the beam of light, said primary pattern having a pattern of transparent and non-transparent portions which is observed by the patient's eye to result in a reflected image of the primary pattern, a pair of analyzer patterns, one of said analyzer patterns having a pattern which substantially corresponds to the pattern of said primary pattern to admit the in-focus reflected image and the other of said analyzer patterns having a pattern which is the negative mirror image of the pattern of said one analyzer pattern to block the in-focus reflected image, and reflection means for transmitting the reflected image of the primary pattern from the patient's eye to said pair of analyzer patterns;

photoelectric means associated with each of said analyzer patterns for detecting the reflected image passing through each of said analyzer patterns to generate light responsive signals; and signal detection means connected to said photoelectric means for detecting the difference in the light responsive signals of said photoelectric means for generating an output signal determinative of the visual acuity of the patient's eye.

2. A visual acuity device according to claim 1 wherein said light source means is a pulsating light source for generating a pulsating beam of light.

3. A visual acuity device according to claims 1 or 2 wherein said light source means comprises an infrared light source and said photoelectric means comprises infrared photodiodes.

4. A visual acuity device according to claim 3 wherein said infrared light source comprises a strobe light and an infrared filter.

5. A visual acuity device according to claim 4 wherein said infrared light source further comprises flash circuit means connected to said strobe light for periodically flashing said strobe light.

6. A visual acuity device according to claim 2 for measuring far vision visual acuity of the patient's eye wherein said pulsating light source comprises an infrared light source and said optical means further comprises a collimating lens in the optical path of the beam of light to generate parallel light rays which make the primary pattern appear at optical infinity and a compensating lens in the optical path of the reflected image to make the reflected image appear at optical infinity.

7. A visual acuity device according to claim 6 wherein said compensating lens is adjustable to determine the far vision visual acuity of the patient's eye in response to the position of said compensating lens at the maximum signal strength of the output signal of said signal detection means.

8. A visual acuity device according to claim 6 wherein said optical means further comprises a lens set positioned adjacent the patient's eye, said lens set having a plurality of lenses which can be inserted in the optical path of the beam of light near the patient's eye so that the far vision visual acuity of the patient's eye can be determined by observing the output signal of said signal detection means in relation to different combinations of said plurality of lenses.

9. A visual acuity device according to claim 6 wherein said optical means further comprises a plurality of different primary patterns individually inserted in the optical path of the beam of light so that the far vision visual acuity of the patient's eye can be determined by observing the output signal of said signal detection means in relation to different ones of said plurality of primary patterns.

10. A visual acuity device according to claim 6 wherein said signal detection means comprises measuring means for measuring the signal strength of the output signal and display means connected to said measuring means for displaying the signal strength of the output signal, the signal strength of the output signal corresponding to the far vision visual acuity of the patient's eye.

11. A visual acuity device according to claim 10 further comprising automatic level control means responsive to the size of the pupil of the patient's eye for minimizing the effect of pupil size on the signal strength of the output signal.

12. A visual acuity device according to claim 11 wherein said signal detection means comprises an automatic gain control amplifier having a gain control input and said automatic level control means comprises infrared detection means connected to the gain control input of said gain control amplifier and responsive to the infrared light reflected by the patient's eye for generating a gain control signal corresponding to pupil size to adjust the gain of said automatic gain control amplifier.

13. A visual acuity device according to claims 1 or 2 for measuring the near vision visual acuity of the patient's eye wherein the distance between said primary pattern and the patient's eye corresponds to the distance between the patient's eye and said pair of analyzer patterns, the distance being approximately the normal reading distance.

14. A visual acuity device according to claim 13 wherein said optical means further comprises a lens set adjacent the patient's eye, said lens set having a plurality of lenses which can be inserted in the optical path of the beam of light near the patient's eye so that the near vision visual acuity of the patient's eye can be determined by observing the output signal of said signal detection means in relation to different combinations of said plurality of lenses.

15. A visual acuity device according to claim 13 wherein said optical means further comprises a plurality of different primary patterns individually inserted in the optical path of the beam of light so that the near vision visual acuity of the patient's eye can be determined by observing the output signal of said signal detection means in relation to different ones of said plurality of primary patterns.

16. A visual acuity device according to claim 13 wherein said signal detection means comprises measuring means for measuring the signal strength of the output signal and display means connected to said measuring means for displaying the signal strength of the output signal, the signal strength of the output signal corresponding to the near vision visual acuity of the patient's eye.

17. A visual acuity device according to claim 16 further comprising automatic level control means responsive to the size of the pupil of the patient's eye for minimizing the effect of the pupil size on the signal strength of the output signal.

18. A visual acuity device according to claim 17 wherein said signal detection means comprises an automatic gain control amplifier having a gain control input and said automatic level control means comprises infrared detection means connected to the gain control input of said gain control amplifier and responsive to the infrared light reflected by the patient's eye for generating a gain control signal corresponding to the pupil size to adjust the gain of said automatic gain control amplifier.

19. A visual acuity device according to claim 1 wherein said optical means further comprises a fixation cross adjacennt said primary pattern.

20. A visual acuity device according to claim 1 wherein said reflection means further comprises first beam splitter means for directing the reflected image from the patient's eye along an optical path different than the optical path of the pulsating beam of light and second beam splitter means adjacent said pair of analyzer patterns for splitting the reflected image between said pair of analyzer patterns.

21. A visual acuity device according to claim 20 wherein said first beam splitter means has a first surface facing the patient's eye to direct the reflected image toward said second beam splitter means and a second surface facing said light source means, said optical means further comprising anti-reflection means positioned relative to said second surface of said first beam splitter means for absorbing glare.

22. A visual acuity device according to claim 1 wherein said optical means further comprises a first and second lens associated with said analyzer patterns to direct the reflected image to said photoelectric means.

23. A visual acuity device according to claim 1 wherein said primary pattern is a radial pattern having a number of transparent radial portions alternating with a like number of non-transparent radial portions, the area of all of said transparent radial portions being approximately 50% of the total area of said radial pattern, said one analyzer pattern being a radial pattern substantially corresponding to the radial pattern of said primary pattern.

24. A visual acuity device according to claim 23 wherein the radial angle of the transparent radial portions of said one analyzer pattern is slightly less than the radial angle of the transparent radial portions of said primary pattern.

25. A visual acuity device according to claim 1 wherein said primary pattern is an equal area pattern having a number of groups of transparent and non-transparent portions, the area of each of said groups being substantially equal, each group having a number of transparent and non-transparent portions, the size of the transparent and non-transparent portions being different for each group in order to provide a wide range for measuring the visual acuity of the patient's eye.

26. A visual acuity device according to claim 2 wherein said signal detection means comprises a differential amplifier having an input connected to each of said photoelectric means to detect the difference signal between said inputs to thereby cancel out glare and provide an output signal representative of the in-focus reflected image of the primary pattern.

27. A visual acuity device according to claim 26 wherein said signal detection means further comprises a peak hold detector connected to said differential amplifier and a DC voltmeter connected to said peak hold detector to display the signal strength of the output signal of said differential amplifier.

28. A visual acuity device according to claim 26 wherein said signal detection means further comprises a filter connected to said differential amplifier and an AC voltmeter connected to said filter to display the signal strength of the output signal of said differential amplifier.

29. A visual acuity device according to claim 26 wherein said signal detection means further comprises a peak hold detector connected to said differential amplifier, an analog/digital converter connected to said peak hold detector and digital display means connected to said analog/digital converter for providing a digital display of the signal strength of the output signal of said different amplifier.

30. A visual acuity device according to claim 1 wherein said optical means comprises removable lens means for converting said visual acuity device from a near vision visual acuity device for measuring near vision to a far vision visual acuity device for measuring far vision.

31. A method for measuring the visual acuity of a patient's eye comprising the steps of:
    directing a pulsating beam of infrared light into the patient's eye through a primary pattern having a pattern of transparent and opaque portions;
    transmitting the reflected image of the primary pattern in the patient's eye through a pair of fixed analyzer patterns, one of said analyzer patterns having a pattern which substantially corresponds to said primary pattern to admit the in-focus reflected image and the other of said analyzer patterns having a pattern which is the negative mirror image of the pattern of said one analyzer pattern to block the in-focus reflected image;
    detecting the light from the reflected image passed by each of said analyzer patterns and converting the light to an electrical signal with photoelectric devices; and
    generating an output signal indicative of the visual acuity of the patient's eye from the electrical signals provided by the photoelectric devices.

32. The method of claim 31 wherein the generating step further comprises the step of measuring the difference between the electrical signals provided by the photoelectric devices.

33. The method of claim 31 wherein the output signal is indicative of the near vision visual acuity of the patient's eye.

34. The method of claim 31 wherein the directing step further comprises the step of transmitting parallel light rays to the patient's eye so that the primary pattern appears at optical infinity, wherein the output signal is indicative of far vision visual acuity.

* * * * *